United States Patent
Siegert et al.

(10) Patent No.: US 8,530,678 B2
(45) Date of Patent: Sep. 10, 2013

(54) TRIOXANE PRODUCTION METHOD WHEREIN A SIDE AQUEOUS FLOW IS DEDUCTED AT A FIRST DISTILLATION STAGE

(75) Inventors: Markus Siegert, Heidelberg (DE); Neven Lang, Mannheim (DE); Eckhard Stroefer, Mannheim (DE); Achim Stammer, Freinsheim (DE); Thorsten Friese, Mannheim (DE)

(73) Assignee: BASF Aktiengesellschaft (DE)

( * ) Notice: Subject to any disclaimer, the term of this patent is extended or adjusted under 35 U.S.C. 154(b) by 1206 days.

(21) Appl. No.: 11/665,840

(22) PCT Filed: Oct. 20, 2005

(86) PCT No.: PCT/EP2005/011303
§ 371 (c)(1),
(2), (4) Date: Apr. 19, 2007

(87) PCT Pub. No.: WO2006/042759
PCT Pub. Date: Apr. 27, 2006

(65) Prior Publication Data
US 2007/0293689 A1      Dec. 20, 2007

(30) Foreign Application Priority Data
Oct. 20, 2004   (DE) .......................... 10 2004 051 118

(51) Int. Cl.
*C07D 323/06*   (2006.01)
(52) U.S. Cl.
USPC .......................................................... 549/368

(58) Field of Classification Search
USPC .......................................................... 549/368
See application file for complete search history.

(56) References Cited

U.S. PATENT DOCUMENTS

| | | | |
|---|---|---|---|
| 3,378,468 A * | 4/1968 | Langecker ....................... 203/44 |
| 4,493,752 A * | 1/1985 | Naito et al. ..................... 203/71 |
| 5,061,349 A | 10/1991 | Kuppenbender et al. |
| 5,766,424 A | 6/1998 | Arnold et al. |
| 6,200,429 B1 | 3/2001 | Freyhof et al. |
| 6,201,136 B1 | 3/2001 | Reichl et al. |
| 6,433,194 B1 | 8/2002 | Schweers et al. |
| 2006/0058537 A1 | 3/2006 | Haubs et al. |

FOREIGN PATENT DOCUMENTS

| | | |
|---|---|---|
| CA | 2549897 | 7/2005 |
| DE | 1668867 | 12/1971 |
| DE | 19526307 | 1/1997 |
| DE | 19732291 | 1/1999 |
| DE | 10361516 | 7/2005 |
| EP | 0133669 | 3/1985 |
| EP | 1000942 | 5/2000 |
| WO | WO-0017188 | 3/2000 |
| WO | WO-2004/054998 | 7/2004 |
| WO | WO-2005/063733 | 7/2005 |

\* cited by examiner

*Primary Examiner* — Andrew D Kosar
*Assistant Examiner* — Raymond Covington
(74) *Attorney, Agent, or Firm* — Novak Druce Connolly Bove + Quigg LLP

(57) ABSTRACT

Processes are disclosed comprising: (a) reacting an aqueous formaldehyde solution in a reactor in the presence of a suitable catalyst to obtain a reaction product mixture comprising trioxane, formaldehyde and water; (b) distilling the reaction product mixture to form a top stream comprising crude trioxane; and (c) treating the top stream in one or more additional stages to form pure trioxane; wherein an aqueous sidestream is drawn off during the distilling of the reaction mixture.

20 Claims, 1 Drawing Sheet

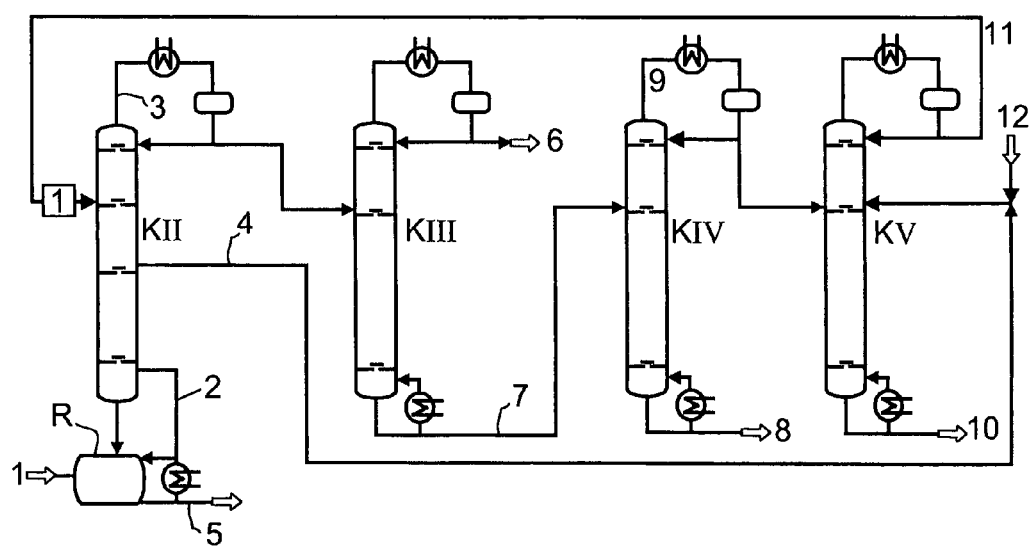

TRIOXANE PRODUCTION METHOD WHEREIN A SIDE AQUEOUS FLOW IS DEDUCTED AT A FIRST DISTILLATION STAGE

CROSS-REFERENCE TO RELATED APPLICATIONS

This application is a national stage application, under 35 U.S.C. §371, of PCT/EP2005/011303, filed Oct. 20, 2005, which claims priority of German Application No. 10 2004 051 118.7, filed Oct. 20, 2004.

BACKGROUND OF THE INVENTION

The invention relates to a process for preparing trioxane from a highly concentrated aqueous formaldehyde solution.

Trioxane is generally prepared by reactive distillation of aqueous formaldehyde solution in the presence of acidic catalysts. The trioxane is subsequently extracted from the distillate comprising formaldehyde and water in addition to trioxane using halogenated hydrocarbons such as methylene chloride or 1,2-dichloroethane, or other water-immiscible solvents.

DE-A 1 668 867 describes a process for removing trioxane from mixtures comprising water, formaldehyde and trioxane by extraction with an organic solvent. In this process, an extraction zone consisting of two subzones is charged at one end with a customary organic, virtually water-immiscible extractant for trioxane, and at the other end with water. Between the two subzones, the distillate of the trioxane synthesis to be separated is fed. On the side of the solvent feed, an aqueous formaldehyde solution is then obtained, and, on the side of the water feed, a virtually formaldehyde-free solution of trioxane in the solvent. In one example, the distillate which is obtained in the trioxane synthesis and is composed of 40% by weight of water, 35% by weight of trioxane and 25% by weight of formaldehyde is metered into the middle section of a pulsation column, and methylene chloride is fed at the upper end of the column and water at the lower end of the column. In this case, an about 25% by weight solution of trioxane in methylene chloride is obtained at the lower end of the column and an about 30% by weight aqueous formaldehyde solution at the upper end of the column.

A disadvantage of this procedure is the occurrence of extractant which has to be purified. Some of the extractants used are hazardous substances (T or T$^+$ substances in the context of the German Hazardous Substances Directive), whose handling entails special precautions.

DE-A 197 32 291 describes a process for removing trioxane from an aqueous mixture which consists substantially of trioxane, water and formaldehyde, by removing trioxane from the mixture by pervaporation and separating the trioxane-enriched permeate by rectification into trioxane and an azeotropic mixture of trioxane, water and formaldehyde. In the example, an aqueous mixture consisting of 40% by weight of trioxane, 40% by weight of water and 20% by weight of formaldehyde is separated in a first distillation column under standard pressure into a water/formaldehyde mixture and into an azeotropic trioxane/water/formaldehyde mixture. The azeotropic mixture is passed into a pervaporation unit which comprises a membrane composed of polydimethylsiloxane with a hydrophobic zeolite. The trioxane-enriched mixture is separated in a second distillation column under standard pressure into trioxane and, in turn, into an azeotropic mixture of trioxane, water and formaldehyde. This azeotropic mixture is recycled upstream of the pervaporation stage.

A disadvantage of this procedure is the very high capital costs for the pervaporation unit.

The German patent application DE 103 61 516.4, unpublished at the priority date of the present application, discloses a process for distillatively removing trioxane from trioxane/formaldehyde/water mixtures which does not need extraction or pervaporation steps. However, the process requires a plant with three distillation columns for the removal of pure dioxane and pure water from the product mixture from a trioxane synthesis reactor.

BRIEF SUMMARY OF THE INVENTION

It is accordingly an object of the invention to improve economic viability of the process, i.e. to carry out the distillative workup of the trioxane/formaldehyde/water mixture from the acid-catalyzed reaction of a highly concentrated aqueous formaldehyde solution with lower energy intensity and higher yield compared to conventional processes.

Accordingly, a process has been found for preparing trioxane, comprising the following process stages:
  acid-catalyzed reaction of a highly concentrated aqueous formaldehyde solution in a reactor to obtain a trioxane/formaldehyde/water mixture (process stage I),
  distillation of the trioxane/formaldehyde/water mixture from process stage I to obtain crude trioxane as the top stream (process stage II) and
  distillative workup of the crude trioxane from process stage II in one or more further process stages to obtain pure trioxane,
which comprises drawing off an aqueous side stream in process stage II.

It has been found that drawing off an aqueous side stream from the distillation column in which the trioxane/formaldehyde/water mixture is removed distillatively from the acid-catalyzed reaction makes possible an operating mode of the distillation column in which the top stream drawn off is crude trioxane which has approximately the composition of the ternary trioxane/formaldehyde/water azeotrope at the top pressure of the column and which is the most economically viable starting basis for the further distillative workup.

DETAILED DESCRIPTION OF THE INVENTION

Process stage I, the reaction of a highly concentrated aqueous formaldehyde solution in a reactor to obtain a trioxane/formaldehyde/water mixture is carried out in a known manner, i.e. under homogeneous or heterogeneous acidic catalysis. The catalysts used are frequently sulfuric acid, methanesulfonic acid, p-toluenesulfonic acid, generally in a concentration of from 5 to 15% by weight, based on the total weight of the aqueous formaldehyde solution, or an equivalent amount of ionic exchange resins or zeolites.

In the present context, highly concentrated refers to an aqueous formaldehyde solution which comprises at least 55% by weight of formaldehyde, or at least 65% by weight of formaldehyde or else 75% by weight of formaldehyde.

In the present context, crude trioxane refers to a stream which comprises trioxane in a proportion by weight of from 60 to 80%, and additionally from 30 to 20% by weight of formaldehyde and from 10 to 30% by weight of water.

Pure trioxane refers to a stream which comprises at least 97.5% by weight, preferably at least 99% by weight or 99.9% by weight or else 99.99% by weight, of trioxane. For polymerizable pure trioxane, specifications are additionally made, depending on the intended use, with regard to the formic acid content (frequently below 2 ppm by weight) and the water content (frequently below 50 ppm by weight).

In the present context, pure water refers to a stream which comprises at least 95% by weight or at least 97.5% by weight or at least 99% by weight, of water.

The trioxane synthesis reactor is in particular a fixed bed or fluidized bed reactor which is operated at superatmospheric pressure. Preference is given to operating the trioxane synthesis reactor at a pressure in the range from 1 to 5 bar absolute. In particular, the operating pressure should not go below a lower limit which corresponds to a temperature at which solid precipitation could take place in the trioxane synthesis reactor.

In order to restrict the yield loss by the formation of the formic acid by-product, the trioxane synthesis reactor is operated preferably at residence times below 30 minutes, more preferably below 15 minutes.

To this end, the highly concentrated aqueous formaldehyde solution in particular fed to the trioxane synthesis reactor via a forced-circulation flash evaporator.

From the upper region of the trioxane synthesis reactor, a gaseous stream comprising trioxane, formaldehyde and water is drawn off. The composition of the gaseous stream from the trioxane synthesis reactor corresponds generally to from 1 to 25% by weight of trioxane, from 50 to 80% by weight of formaldehyde and from 10 to 25% by weight of water.

The gaseous stream from the trioxane synthesis reactor is, preferably via a control valve, decompressed into the downstream column in which the trioxane/formaldehyde/water mixture is separated in process stage II into a top stream comprising crude trioxane and a bottom stream which is preferably recycled into the trioxane synthesis reactor.

This circulation stream is mixed with the freshly fed highly concentrated formaldehyde solution either upstream of the circulation pump or in a reaction mixer. Particularly advantageously, a static mixer may be used for this function. Alternatively, it is also possible to conduct the circulation stream and the fresh aqueous formaldehyde stream each separately and merely immersed into the trioxane synthesis reactor.

The top stream comprising crude trioxane is purified in one or more further process stages distillatively to give pure trioxane.

The pressure differential between the column in which process stage II is carried out and the trioxane synthesis reactor may, alternatively to the control valve, be balanced, for example, by hydrostatic pressure.

Since the trioxane-containing reaction mixture from the trioxane synthesis reactor is drawn off in gaseous form, the acids critical to the solid precipitation of paraformaldehyde remain in the trioxane synthesis reactor and are not entrained into the distillation column. This allows less expensive steel types to be used for the column which do not have to be acid-resistant.

The composition of the crude trioxane drawn off as the top stream in process stage II is determined in such a way that it corresponds to the composition of the ternary trioxane/formaldehyde/water azeotrope at the top pressure of the column because this is the most economically viable starting basis for the further distillative workup.

According to the invention, an aqueous side stream is drawn off in process stage II, preferably in liquid form.

The aqueous side stream comprises advantageously from 10 to 90% by weight, preferably from 40 to 80% by weight, more preferably from 50 to 80% by weight, of water.

Process stage II is carried out advantageously in a column which has from 5 to 40 theoretical plates and is operated at a top pressure between 0.05 and 2.50 bar absolute.

Preference is further given to the column in which process stage II is carried out being designed with from 5 to 20 theoretical plates and being operated at a top pressure between 0.20 and 0.75 bar absolute.

The position of the draw for the aqueous side stream in process stage II is advantageously located at a theoretical plate whose position is between 10% and 90% of the total number of theoretical plates in the column.

Advantageously, the reactor in which process stage I is carried out and the column in which process stage II is carried out are connected to form a unit, in such a way that the vapors rising out of the reactor directly into the column and the liquid effluxing out of the column directly enters the reactor.

In order to prevent the accumulation of high boilers, in the present context dimethoxydimethyl ether and formic acid in particular, a stream of from 0.01 to 1% by weight of the feed amount into the reactor, in particular of from 0.1 to 1.0% by weight of the feed amount into the reactor, is advantageously discharged continuously or batchwise from the reactor in which process stage I is carried out or from the column in which process stage II is carried out.

The further distillative workup of the crude trioxane drawn off in process stage I can preferably be effected in such a way that the crude trioxane is fed to a column in which a stream comprising low boilers is removed, the column advantageously comprising from 5 to 50 theoretical plates and being operated at a top pressure between 0.1 and 5 bar absolute. Preference is further given to the column for the removal of the low boilers being designed with from 10 to 30 theoretical plates and being operated at a top pressure between 1.0 and 2.5 bar absolute.

In the present context, low boilers refer to substances whose boiling point is below the boiling point of pure trioxane; these are in particular methylal, methanol and methyl formate.

The column in which the low boilers are removed is preferably designed in such a way that the rectifying section thereof has from 25 to 95%, preferably from 50 to 75%, of the total number of theoretical plates of the column.

The bottom stream from the column from which the low boilers are drawn off is fed to a trioxane purifying column in which pure trioxane is obtained as a side draw or as a bottom stream. The trioxane purifying column is preferably operated at a top pressure which is from 0.10 to 10.0 bar higher than the top pressure of the column in which process stage II is carried out.

The top stream from the trioxane purifying column is preferably fed to a further column in which the bottom stream drawn off is pure water. This column is preferably designed with from 5 to 50, in particular with from 10 to 30, theoretical plates, and is operated at a top pressure between 1.0 and 10 bar absolute, preferably at a top pressure between 2.5 and 6.5 bar absolute.

The trioxane purifying column and/or the column in which the bottom stream drawn off is pure water is preferably designed in such a way that the stripping section has from 25 to 100%, preferably from 75 to 100%, more preferably from 90 to 100%, of the total number of theoretical plates of the column.

Advantageously, the side stream from the column in which process stage II is carried out and/or a further aqueous stream of the column in which pure water is obtained is fed and/or the top stream from the column in which pure water is obtained is fed to the column in which process stage II is carried out.

The further aqueous stream which is fed to the column in which pure trioxane is obtained preferably does not comprise any components extraneous to the process and preferably has a water content of at least 10% by weight, in particular of at least 50% by weight.

Advantageously, instead of the trioxane purifying column and the column in which pure water is obtained, a dividing wall column may be used in which a bottom stream comprising pure trioxane and a side stream comprising pure water are drawn off.

The invention is illustrated in detail hereinbelow with reference to a drawing.

FIG. 1 shows the schematic representation of a preferred plant according to the invention. A highly concentrated aqueous formaldehyde solution, stream 1, is fed to a reactor R to obtain a trioxane/formaldehyde/water mixture, stream 2. Stream 2 is separated in a column K II into a crude trioxane top stream 3 and an aqueous side stream 4.

The top stream 3 is partly introduced back to the column K II as reflux and otherwise passed to a column K III in which low boilers, stream 6, are removed overhead. The bottom stream 7 from the column K III is fed to a trioxane purifying column K IV in which, in the preferred embodiment shown in the FIGURE, pure trioxane is drawn off as the bottom 8. The top stream 9 from the column K IV is fed to a further column K V in which pure water is drawn off as the bottom stream 10, as is a top stream 11 which, in the preferred embodiment shown in the FIGURE, is recycled into the column K II. The aqueous side stream from the column K II and a further aqueous side stream 12 are fed to the column K V.

What is claimed is:

1. A process comprising:
   (a) reacting an aqueous formaldehyde solution in a reactor in the presence of a suitable catalyst to obtain a reaction product mixture comprising trioxane, formaldehyde and water;
   (b) distilling the reaction product mixture in a column to form a top stream comprising crude trioxane having a ternary trioxane/formaldehyde/water azeotrope composition at the to pressure of the column; and
   (c) treating the top stream in one or more additional stages to form pure trioxane;
   wherein an aqueous sidestream is drawn off during the distilling of the reaction product mixture.

2. The process according to claim 1, wherein the aqueous sidestream comprises a liquid.

3. The process according to claim 1, wherein water is present in the aqueous sidestream in an amount of 10 to 90% by weight.

4. The process according to claim 1, wherein the column has 5 to 40 theoretical plates, and wherein the column is operated at a top pressure of 0.05 and 2.50 bar absolute.

5. The process according to claim 1, wherein the column has 5 to 20 theoretical plates, and wherein the column is operated at a top pressure of 0.20 and 0.95 bar absolute.

6. The process according to claim 1, wherein the column has a number of theoretical plates, and wherein the aqueous sidestream is drawn off at a theoretical plate disposed at a position between 10% and 90% of the theoretical plates.

7. The process according to claim 1, wherein reacting the aqueous formaldehyde solution and distilling the reaction product mixture are carried out in the reactor and the column as a unit such that vapors rising out of the reactor directly enter the column and liquid effluxing out of the column enter directly into the reactor.

8. The process according to claim 1, further comprising discharging a purge stream from the process, in an amount of 0.01 to 1% by weight of the aqueous formaldehyde solution introduced into the reactor; and wherein the purge stream is discharged from one or both of: (i) the reactor during the reacting of the aqueous formaldehyde solution; and (ii) the column in which the distilling of the reaction product mixture is carried out.

9. The process according to claim 1, wherein treating the top stream comprises feeding the top stream to a further column having 5 to 50 theoretical plates and operated at a top pressure of 0.1 to 5.0 bar absolute, such that low boilers are removed overhead.

10. The process according to claim 1, wherein treating the top stream comprises feeding the top stream to a further column having 10 to 30 theoretical plates and operated at a top pressure of 1.0 to 2.5 bar absolute, such that low boilers are removed overhead.

11. The process according to claim 10, wherein the further column has a rectifying section comprising 25 to 95% of the theoretical plates.

12. The process according to claim 1, wherein treating the top stream comprises feeding the top stream to a further column such that low boilers are removed overhead, and a bottom stream from the further column is fed to a second further column operated at a top pressure which is 0.10 to 10.0 bar greater than a top pressure of a column in which the distilling of the reaction product mixture is carried out, such that the pure trioxane is obtained as one or more of a side stream and bottom stream from the second further column.

13. The process according to claim 12, further comprising feeding a top stream from the second further column to a third further column having 5 to 50 theoretical plates and operated at 1.0 to 10.0 bar absolute to form a bottom stream from the third further column comprising pure water.

14. The process according to claim 12, further comprising feeding a top stream from the second further column to a third further column having 10 to 30 theoretical plates and operated at 2.5 to 6.5 bar absolute to form a bottom stream from the third further column comprising pure water.

15. The process according to claim 13, wherein one or both of the second further column and the third further column has a stripping section comprising 25 to 100% of the theoretical plates in the column.

16. The process according to claim 13, further comprising one or more additional feed introductions selected from the group consisting of: feeding the aqueous sidestream from the distilling of the reaction mixture to the third further column, feeding a top stream from the third further column to the distilling of the reaction mixture, and feeding an additional aqueous stream to the third further column.

17. The process according to claim 1, wherein treating the top stream comprises feeding the top stream to a further column such that low boilers are removed overhead, and a bottom stream from the further column is fed to a dividing wall column and distilled therein such that the pure trioxane is obtained as a bottom stream from the dividing wall column and pure water is obtained as a side stream from the dividing wall column.

18. The process according to claim 1, wherein water is present in the aqueous sidestream in an amount of 40 to 80% by weight.

19. The process according to claim 10, wherein the further column has a rectifying section comprising 50 to 75% of the theoretical plates.

20. The process according to claim 13, wherein one or both of the second further column and the third further column has a stripping section comprising 75 to 100% of the theoretical plates in the column.

* * * * *